United States Patent [19]

Brück

[11] 4,003,383
[45] Jan. 18, 1977

[54] APPARATUS FOR LOCALLY IRRADIATING A PART OF A LIVING BODY

[76] Inventor: Gernot Klaus Brück, Hermann-Pfaume-Str. 6, Cologne, Germany

[22] Filed: Nov. 3, 1975

[21] Appl. No.: 628,546

[30] Foreign Application Priority Data

Nov. 4, 1974 Germany .......................... 2452227

[52] U.S. Cl. ................................................ 128/404
[51] Int. Cl.$^2$ ........................................... A61N 5/04
[58] Field of Search ........... 128/404, 405, 422, 413

[56] References Cited

UNITED STATES PATENTS

| | | | |
|---|---|---|---|
| 2,388,830 | 11/1945 | Cotton | 128/404 |
| 2,407,690 | 9/1946 | Southworth | 128/422 |
| 2,413,187 | 12/1946 | McCurdy et al. | 128/404 |
| 2,567,757 | 9/1951 | Argento | 128/404 |

FOREIGN PATENTS OR APPLICATIONS

| | | | |
|---|---|---|---|
| 1,163,992 | 2/1964 | Germany | 128/404 |
| 570,202 | 12/1957 | Italy | 128/404 |
| 464,593 | 5/1949 | Italy | 128/404 |

*Primary Examiner*—Robert W. Michell
*Assistant Examiner*—Lee S. Cohen
*Attorney, Agent, or Firm*—Browdy and Neimark

[57] ABSTRACT

Apparatus for locally treating limited parts of a living body comprising a radiation emitter at the first focus of an ellipsoidal reflective surface with the part to be irradiated at the second focus. The reflective surface is on the interior of a casing which may be formed by a plurality of annular rings which are selectively removed to vary the distance between the radiated part and the radiation exit aperture. The source is preferably coupled to a waveguide, the waveguide and casing being filled with a dielectric.

16 Claims, 1 Drawing Figure

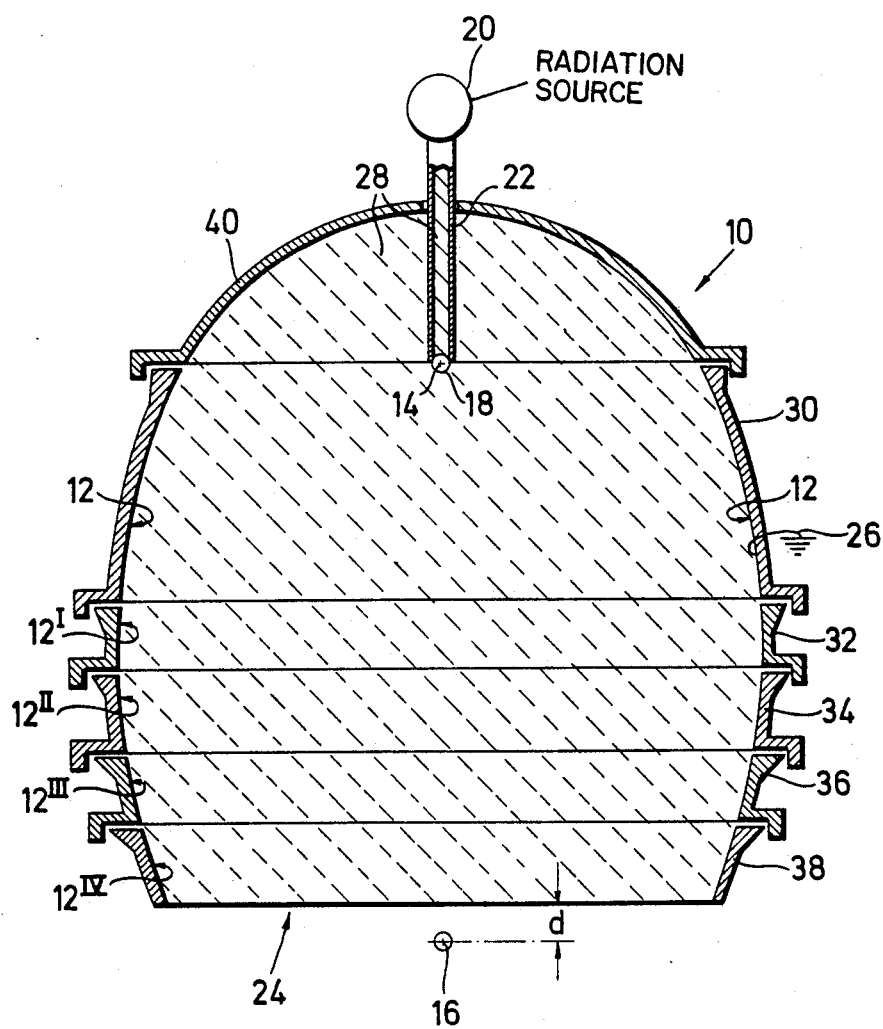

APPARATUS FOR LOCALLY IRRADIATING A PART OF A LIVING BODY

Field of Invention

This invention relates to an apparatus for locally treating limited parts of a human body.

Description of Prior Art

Various methods are known for locally irradiating limited parts of a living body, for example, the so-called "multiple-field irradiation" or "cross-fire irradiation" technique. In multiple-field irradiation a number of smaller fields are used in order to protect the surrounding skin and tissue and to achieve the largest possible depth dose. In cross-fire irradiation, beam cones from different incident fields which overlap at the point which is to be radiated are used. The aim is similarly to achieve a high concentration of radiation at the locally limited point which is to be irradiated, whilst the surrounding area is spared as much as possible.

With irradiation methods known hitherto it is, however, not possible to spare healthy tissue and skin in the region of the diseased focus which is to be irradiated as a locally limited point, particularly when a high concentration of energy is necessary at the focus itself in order to destroy the diseased tissue. With known methods of irradiation, impairment of or even serious damage to the surrounding healthy tissue and skin cannot be precluded.

Summary of Invention

The invention seeks to provide an apparatus for locally irradiating a part of a living body wherein a limited focus of disease can be irradiated without a substantial risk of injury to the surrounding healthy tissue and skin. In its broadest aspect, the invention essentially comprises a casing with a radiation reflective internal surface, the casing surrounding a radiation emmission point which may be coupled, for example, through a waveguide to a radiation source. The casing has an elliptic cross-section and the radiation emmission point is located at a first focus thereof. The part to be irradiated may thereby be positioned beneath an outlet aperture of the casing so that a focus of disease may be located at the second focus of the elliptic radiation reflective surface. The reflective surface is preferably ellipsoidal so that the radiation emitted at the first focus is reflected by said surface and concentrated at the second surface at the site of the disease which is to be irradiated. Thereby, almost the entire energy of the radiation from the first focus is concentrated at the site of the disease. As the energy concentration decreases with the third power of distance, the surrounding healthy tissue and skin receives only radiation of greatly reduced energy so that it is substantially undamaged.

Preferably, radiation having a wave length of from 0.1mm – 100mm, and preferably between 10mm – 100mm, is used because such radiation can be highly focused and thus concentrated precisely at the second focus of the ellipsoidal radiation reflective surface. Furthermore, radiation within this preferred wave length will penetrate to the required depth in a living body and be absorbed to such an extent that, at the second focus of the reflective surface, a sufficiently high concentration of energy is achieved to destroy the diseased tissue. The wave length used in each particular case is selected with regard to the required depth of penetration and radiation absorbtion. Since the radiation passing through the body outside the second focus is not concentrated, substantial damage to this tissue and the skin is avoided.

In a preferred embodiment, the casing comprises a series of rings which are detachably joined together. The interior surface of each ring is an annular band which forms part of the ellipsoidal reflective surface. The rings may be selectively removed to vary the distance between the second focus and a radiation exit aperture of the casing. Preferably, the casing is subdivided approximately from a central plane between the two foci, the reflective surface extending around the first focus towards the radiation exit aperture. In such an arrangement, the rings are detached to give the optimum approximation to the shortest distance between the diseased site and the skin of the body. Although less radiation will be reflected from said surface as more rings are detached, energy is still concentrated at the diseased site to give the advantages described above.

Preferably, the radiation reflective surface is conductive and is electrically connected to an earth wire. An optimum reflection factor is thereby achieved.

A waveguide, filled with a dielectric, can be disposed between a radiation source and the first focus of the ellipsoidal reflective surface. An advantage of this arrangement is that the cross-section of the bundle of rays passing from the first focus can be optimised by suitably selecting the dielectric constant of the dielectric in the waveguide depending on the local spread of the diseased site which is to be irradiated. The narrower the cross-section of the bundle, the less will be the blurring of the radiation concentrated at the second focus. The cross-sectional area of the part of the living body irradiated with a high concentration of radiation depends directly on the cross-section of the bundle of rays passing from the first focus. Advantageously, the interior of the casing is filled with a dielectric having a dielectric constant equal to, or as close as possible to the dielectric constant of a living body. This avoids radiation refraction at transition surfaces so that the radiation is accurately concentrated at the second focus. The outlet aperture of the waveguide at the first focus is preferably in the form of a horn radiator.

Therefore, it is an objection of this invention to provide apparatus for locally irradiating a part of a living body wherein a diseased site can be treated without substantial risk of injury to surrounding healthy tissue and skin.

It is a further object of the invention to provide such an apparatus where the energy of radiation is optimally concentrated at the diseased site.

It is another object of the invention to provide apparatus wherein the distance between a diseased site and a radiation outlet aperture can be easily adjusted.

It is yet a further object of the invention to provide apparatus wherein radiation of an optimum wave length can be used in an effective manner.

Further objects and advantages of the invention will become apparent from the following description of a preferred embodiment.

Description of Drawings

FIG. 1 is a cross sectional view of apparatus, according to the invention, for locally irradiating a living body.

Description of Preferred Embodiments

Referring to FIG. 1, a casing 10 is provided with an ellipsoidal radiation reflective surface 12 which forms rather more than two-thirds of a complete ellipsoid. The upper portion of the casing 10 comprises a wide ring 30 and a cap 40 which is disposed on the ring 30 and has an interior forming one end of the ellipsoidal reflective surface 12.

On the side of the wide casing ring 30 remote from the casing cap 40 are connected a multiplicity of small casing rings 32, 34, 36 and 38, which are disposed close to one another in a detachable manner. The abutting edges of the individual casing parts are so shaped that when the parts are assembled the ellipsoid reflective surface formed inside the casing 10 is interrupted as little as possible.

The ellipsoid reflective surface 12 provided inside the casing 10 forms two focal points, namely a first focal point 14 and a second focal point 16. While the first focal point 14 is disposed, inside the casing, in the region of the end face of the casing cap 40, the second focal point 16 lies outside the last casing ring 38 of the multiplicity of small casing rings.

A waveguide 22 is guided through an opening in the apex of the casing cap 40 to the first focal point 14. Such outlet of the waveguide 22 may be in the form of a horn radiator. On the end of the waveguide 22 lying outside the casing 10 a radiation source 20, which may be an ultrasonic transducer, is disposed, while the end of the waveguide 22 lying at the first focal point 14 of the ellipsoid reflective surface 12 has an outlet aperture 18 for the radiation.

Both the waveguide 22 and the entire casing are filled with a dielectric 28, whose dielectric constant is as far as possible equal to the dielectric constant of a living body.

The end face of each of the small casing rings, 32, 34 36, and 38 which is remote from the first focal point 14 of the ellipsoid reflective surface 12 forms a beam passage aperture 24.

The ellipsoid reflective surface 12 is made electrically conductive and is electrically connected to an earth wire 26.

When all parts of the casing 10 shown in the drawing have been assembled, the casing 10 forms in its interior an ellipsoid reflective surface 12, 12', 12'', 12''', 12'''' which forms an ellipsoid of rotation which is complete except for the bottom ellipsoid cap extending around the second focal point 16.

When the apparatus shown in the drawing is used, the distance between the diseased focus which is to be irradiated in a living body and the skin surface of the latter on which the apparatus can be placed is first determined. As many small casing rings 38, 36, 34, 32 are then removed from the casing 10 as are required to make the distance between the second focal point 16 and the beam passage aperture 24 of the next casing ring which has not been removed correspond as closely as possible to the previously determined distance in the living body. The apparatus is then placed on the living body in such a manner that the second focal point 16 coincides as accurately as possible with the disease focus which is to be irradiated. The disease focus which is to be irradiated is then irradiated with an energy radiation of preselected wavelength and intensity for a predetermined period of time. By this means high energy absorption in the disease focus itself is achieved, while the surrounding healthy tissue does not suffer because the concentration of energy decreases from the second focal point with the third power of the distance.

The invention is defined by the following claims.

I claim:

1. Apparatus for locally irradiating a part of a living body, the apparatus comprising means for emitting radiation from a point, a casing surrounding said radiation emission point, said casing being positionable above a body in the region of the part requiring treatment, and having an interior provided with a surface capable of reflecting radiation from said emission point, said surface being greater than half an ellipsoid, said emission point being within said casing arranged at a first focus point of said ellipsoid whereby said part to be irradiated is positionable at the second focus point of said ellipsoid outside said casing to receive focused radiation reflected from said surface.

2. Apparatus according to claim 1 wherein said casing comprises rings, said rings being detachably joined together and having inner annular surfaces forming said reflective surface whereby said rings can be removed to vary the distance between said first focus point and a radiation exit aperture of said casing.

3. Apparatus according to claim 2 wherein the casing is subdivided approximately from a central plane between the two foci into said rings.

4. Apparatus according to claim 1 further comprising an earth wire, and wherein said reflective surface is conductive and is electrically connected to said earth wire.

5. Apparatus according to claim 1 wherein the interior of said casing is filled with a dielectric.

6. Apparatus according to claim 1 wherein the means for emitting radiation from a point includes a waveguide provided to conduct radiation from a source outside of said casing to said emission point, the waveguide having an outlet aperture located at said first focus point.

7. Apparatus according to claim 6 wherein the waveguide is filled with a dielectric.

8. Apparatus according to claim 7 wherein the outlet aperture of the waveguide is in the form of a horn radiator.

9. Apparatus according to claim 1 wherein the interior of said casing is filled with a dielectric and wherein the means for emitting radiation from a point includes; a waveguide provided to pass radiation from a radiation source outside of said apparatus to said emission point, the waveguide having an outlet aperture located at said first focus point and said waveguide also being filled with the dielectric, the dielectric constant of said dielectric being substantially equal to the dielectric constant of the part to be irradiated.

10. Apparatus according to claim 1 further comprising radiation source means for providing radiation to said emission point, said radiation source means providing radiation with a wavelength of from 0.1 to 100mm.

11. Apparatus according to claim 10 wherein said radiation source means which provides radiation with a wavelength of from 10 to 100mm.

12. Apparatus according to claim 1 further comprising radiation source means for providing radiation to said emission point, said radiation source means comprising an ultrasonic transmitter.

13. Apparatus for locally irradiating a part of a living body, the appartus comprising casing means, said casing means being interiorly provided with a radiation reflective surface defining more than half an ellipsoid, radiation guidance means, said radiation guidance means having an emission aperture located at a first focus of said ellipsoidal shaped radiation reflective surface, said casing means having a radiation exit aperture located between said first focus and the second focus of said ellipsoidal shaped radiation reflective surface, said casing means and said radiation guidance means being filled with a dielectric having a dielectric constant substantially the same as the dielectric constant of the body to be irradiated, said reflective surface being conductive, and means to ground said reflective surface, whereby said part to be irradiated is positionable at said second focus to receive focussed radiation reflected from said surface.

14. Apparatus according to claim 13 wherein said casing means comprises a series of annular rings which are detachably joined together whereby said rings can be selectively removed to vary the distance between said first focus and said radiation exit aperture of said casing means.

15. Apparatus according to claim 14 including radiation source means for passing radiation of wavelength in the range of from 0.1 to 100mm to said radiation guidance means.

16. Apparatus according to claim 15 wherein said radiation source means includes an ultrasonic transducer.

* * * * *